United States Patent [19]
Wyrick

[11] Patent Number: 5,833,669
[45] Date of Patent: Nov. 10, 1998

[54] MEDICINE INJECTION SYRINGE CONSTRUCTIONS

[75] Inventor: Ronald E. Wyrick, Spokane, Wash.

[73] Assignee: Washington Biotech Corp., Spokane, Wash.

[21] Appl. No.: 491,041

[22] Filed: Jun. 16, 1995

Related U.S. Application Data

[63] Continuation-in-part of Ser. No. 243,641, May 16, 1994, Pat. No. 5,540,664, which is a continuation-in-part of Ser. No. 68,644, May 27, 1993, Pat. No. 5,358,489, which is a continuation-in-part of Ser. No. 262,744, Jun. 20, 1994, abandoned.

[51] Int. Cl.⁶ .................................................. A61M 5/00
[52] U.S. Cl. ........................ 604/234; 604/232; 604/208
[58] Field of Search .................................. 604/207, 208, 604/210, 211, 232, 234

[56] References Cited

U.S. PATENT DOCUMENTS

| | | |
|---|---|---|
| 3,770,026 | 11/1973 | Isenberg .................................. 604/208 |
| 3,811,441 | 5/1974 | Sarnoff ..................................... 604/234 |
| 4,073,321 | 2/1978 | Moskowitz ............................... 604/208 |
| 4,091,812 | 5/1978 | Helixon et al. .......................... 604/208 |
| 4,112,945 | 9/1978 | Helixon et al. .......................... 604/208 |
| 4,153,056 | 5/1979 | Silver et al. ............................. 604/211 |
| 4,444,335 | 4/1984 | Wood et al. ............................. 604/208 |
| 4,642,103 | 2/1987 | Gettig . | |

*Primary Examiner*—Richard J. Apley
*Assistant Examiner*—Benjamin K. Koo
*Attorney, Agent, or Firm*—Wells, St. John, Roberts, Gregory & Matkin, P.S.

[57] ABSTRACT

Converters for use with commercially available syringe cartridges to produce novel syringe assemblies. The converters engage with the plunger end of the syringe cartridge. The converter has a body piece with a receptacle. The ampule of a syringe cartridge is inserted into and secured within the receptacle. A plunger shaft allows manual displacement of the plunger. In some embodiments, dose regulating features are preferably included as part of the converter assembly. In one form the dose regulating features include removable collars.

36 Claims, 10 Drawing Sheets

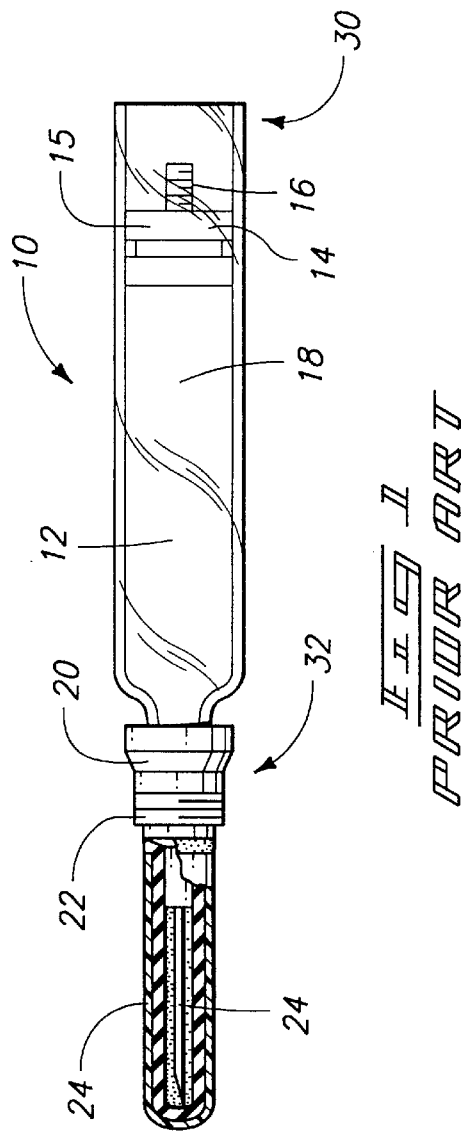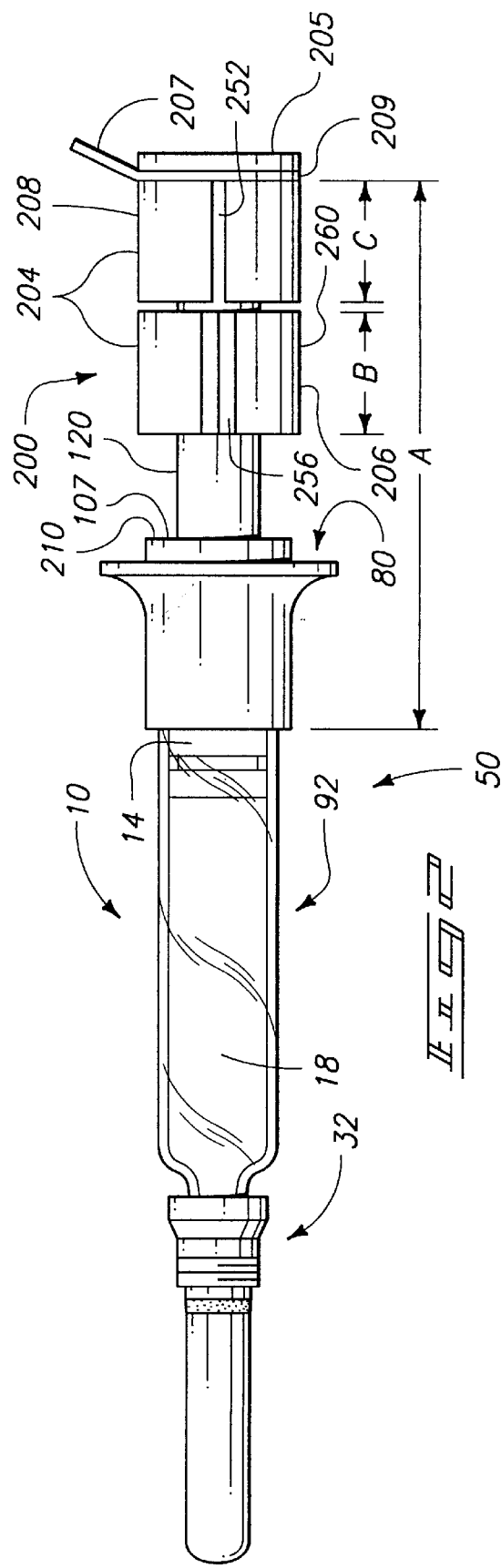

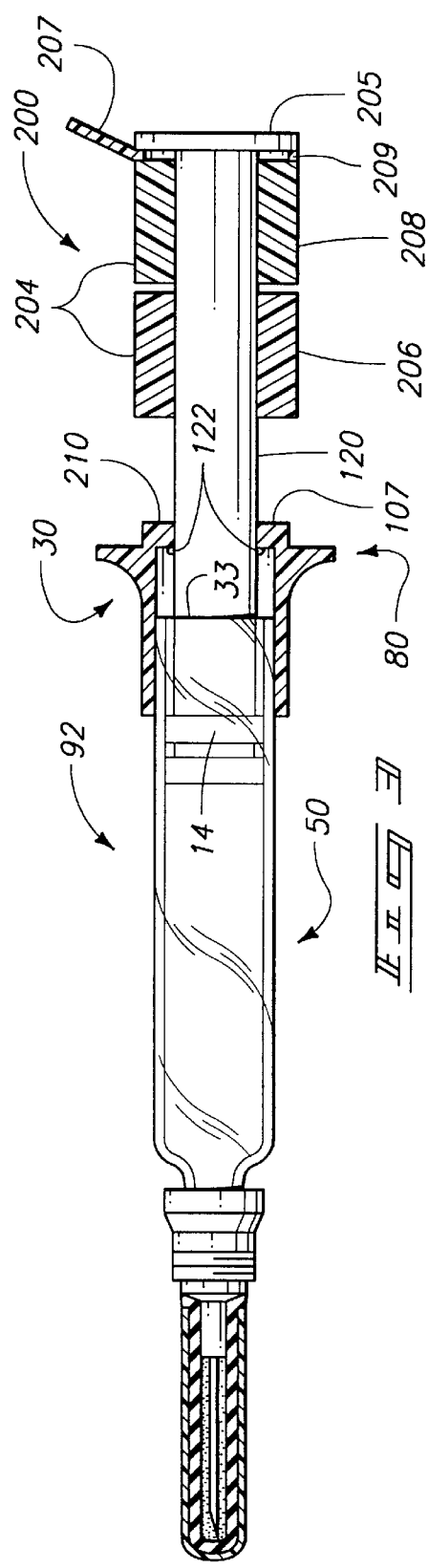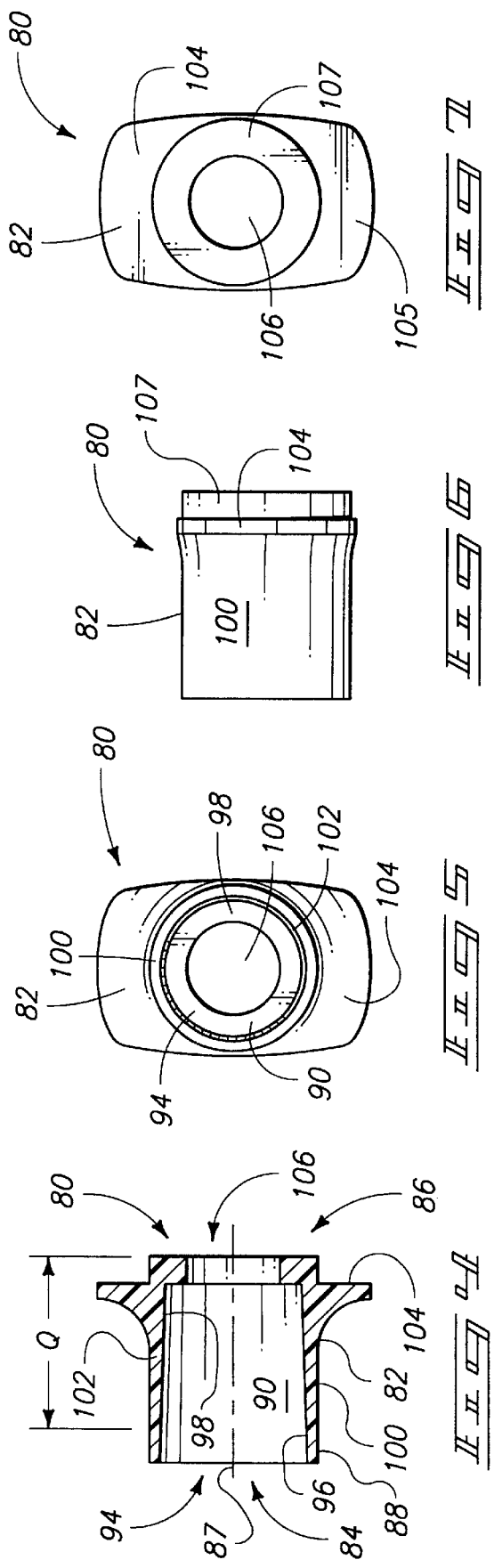

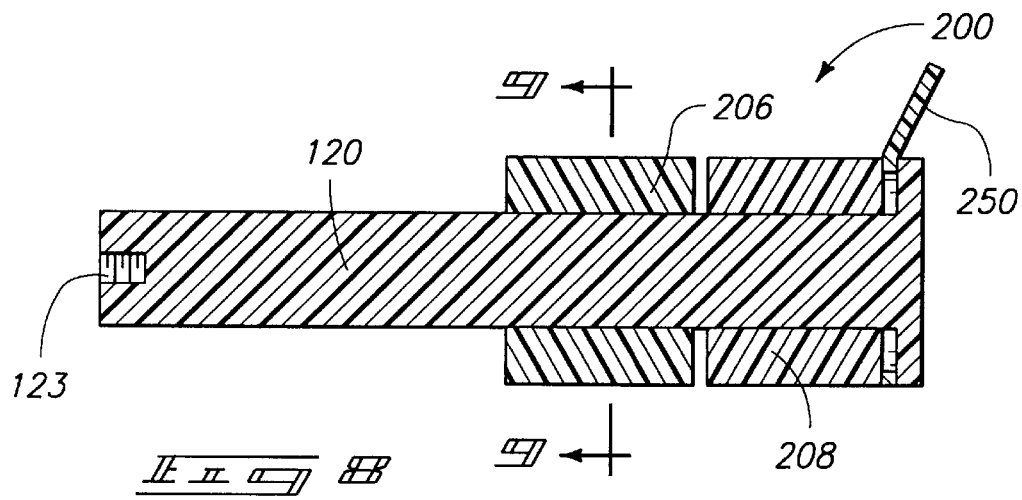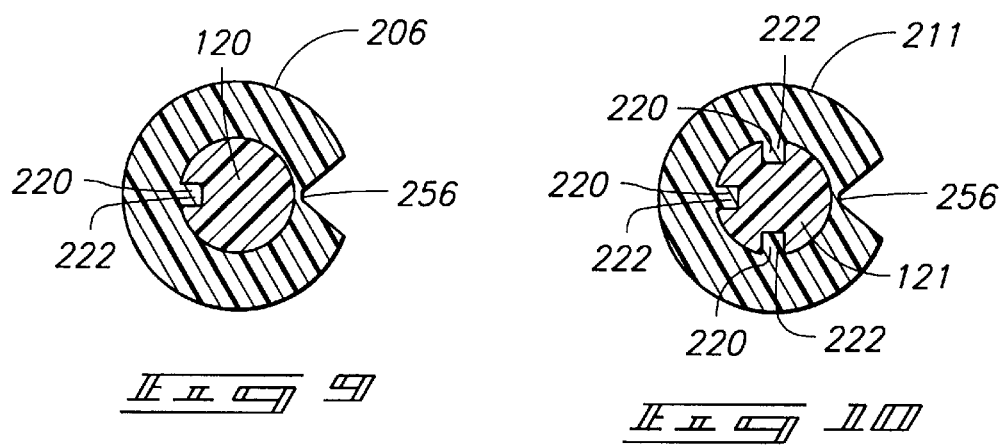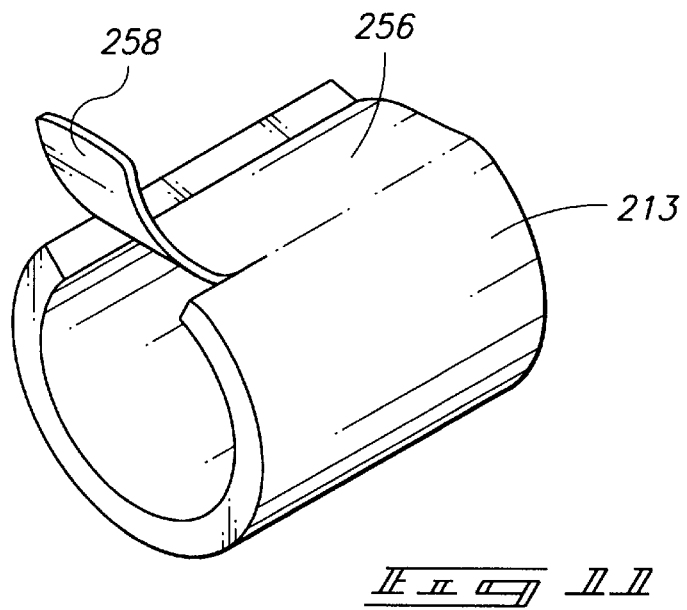

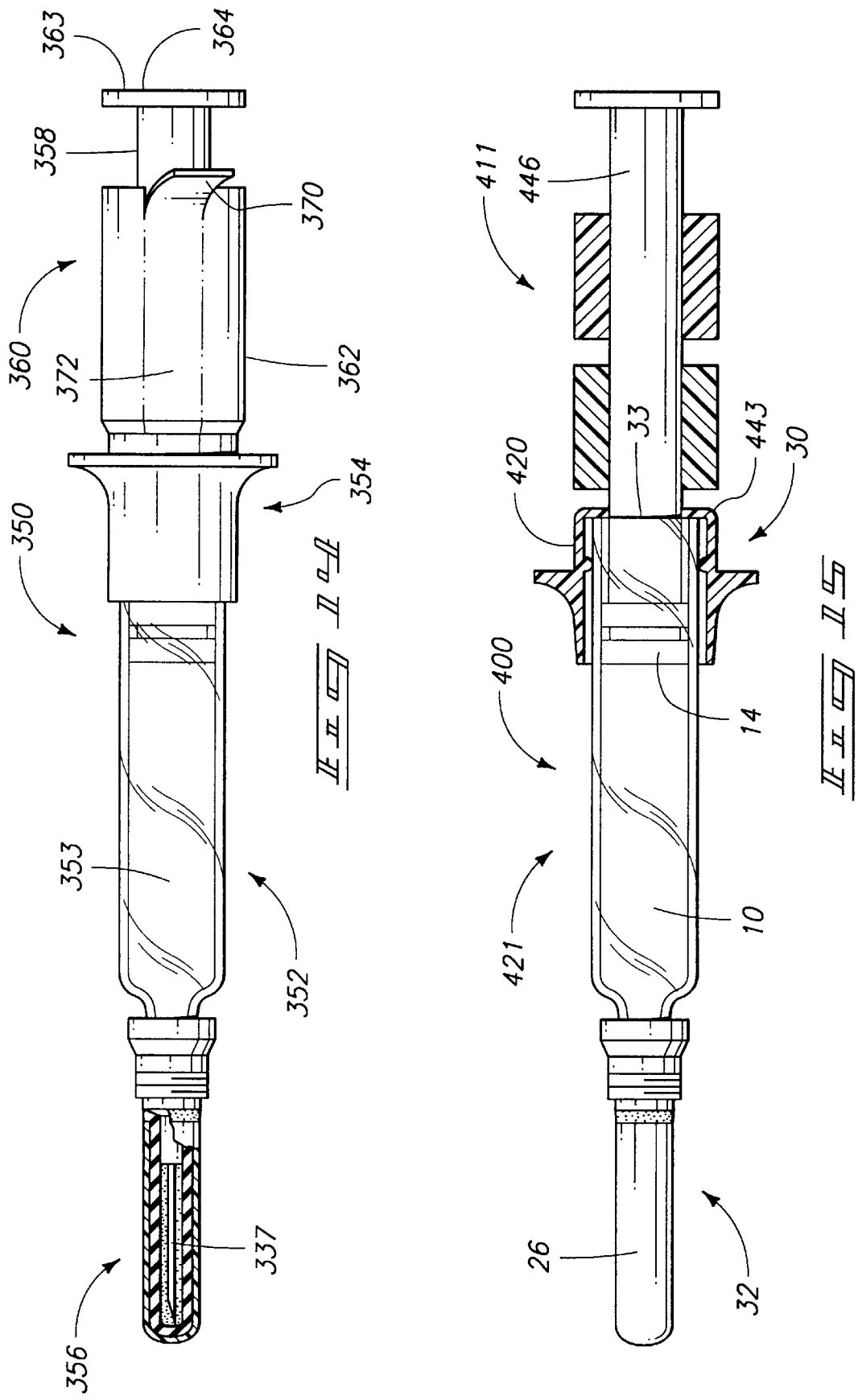

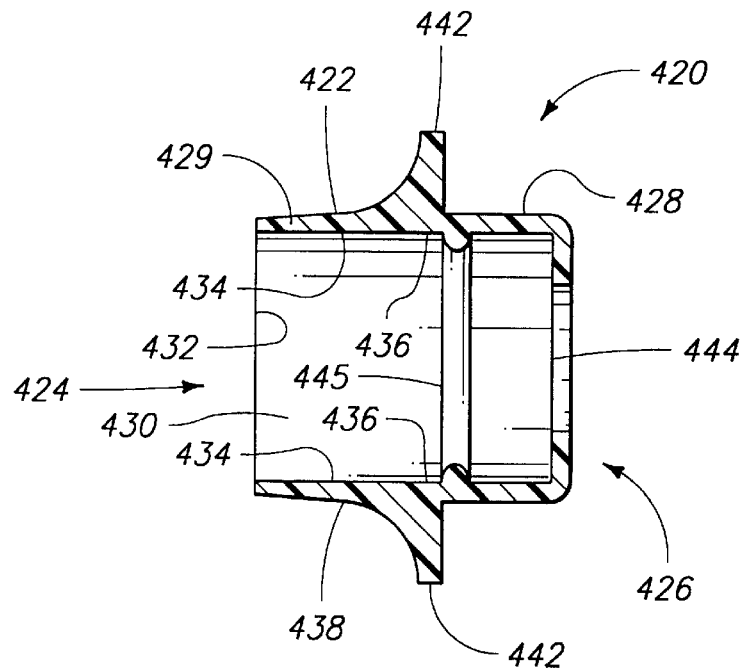
_FIG 16_
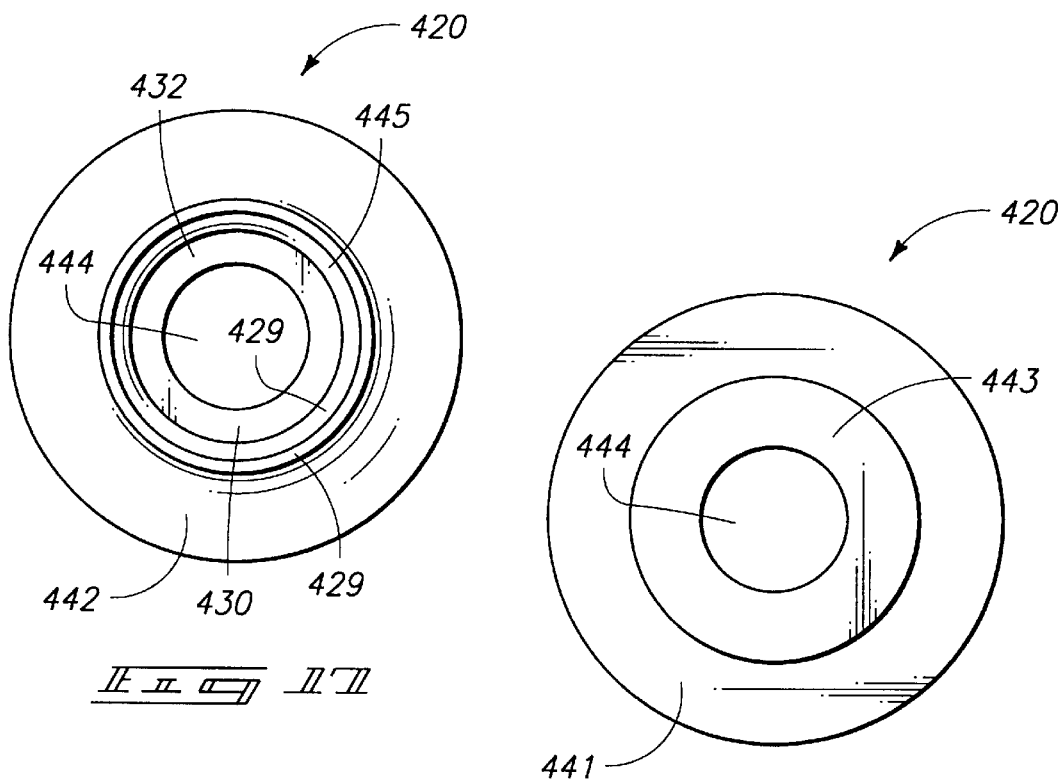
_FIG 17_    _FIG 18_

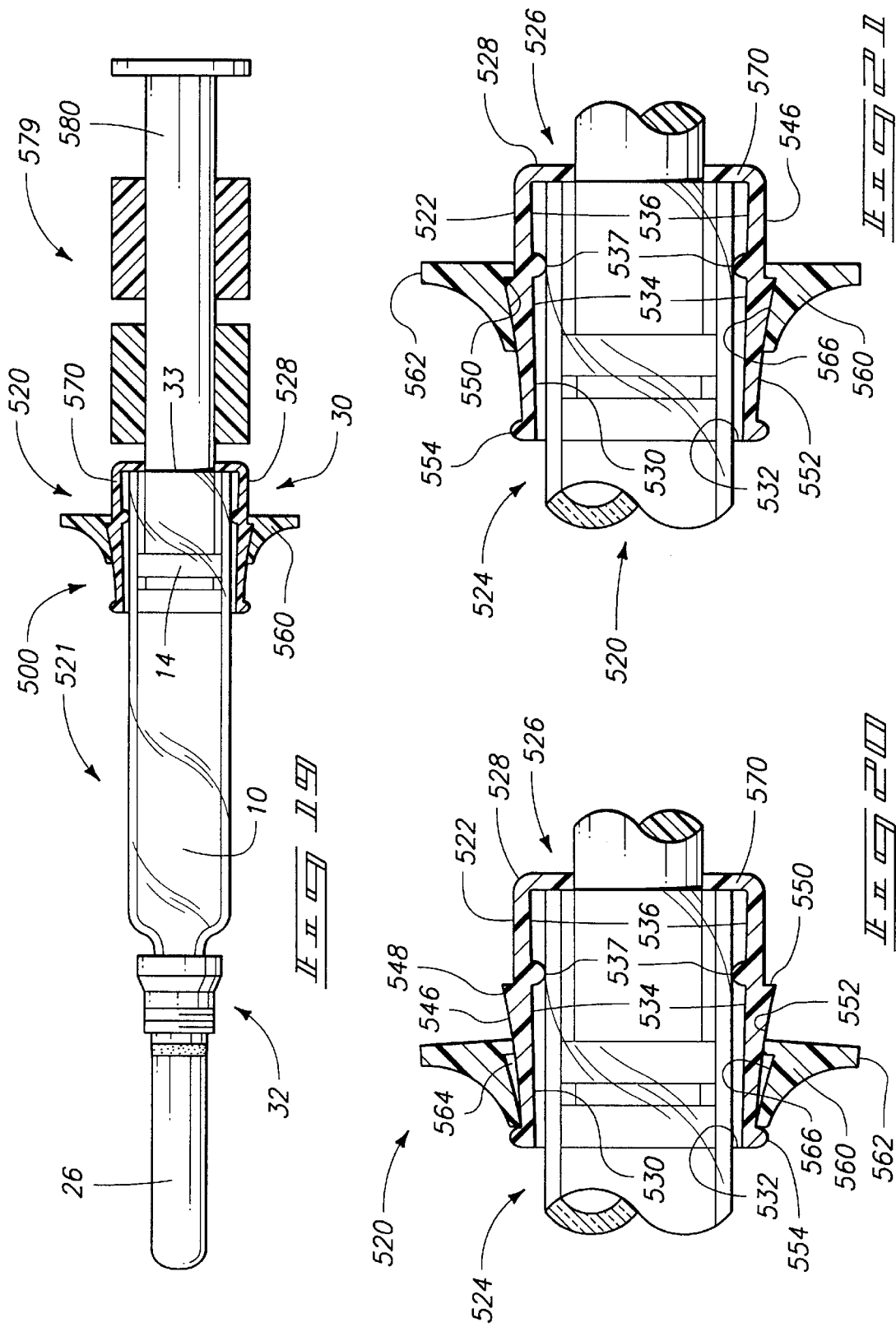

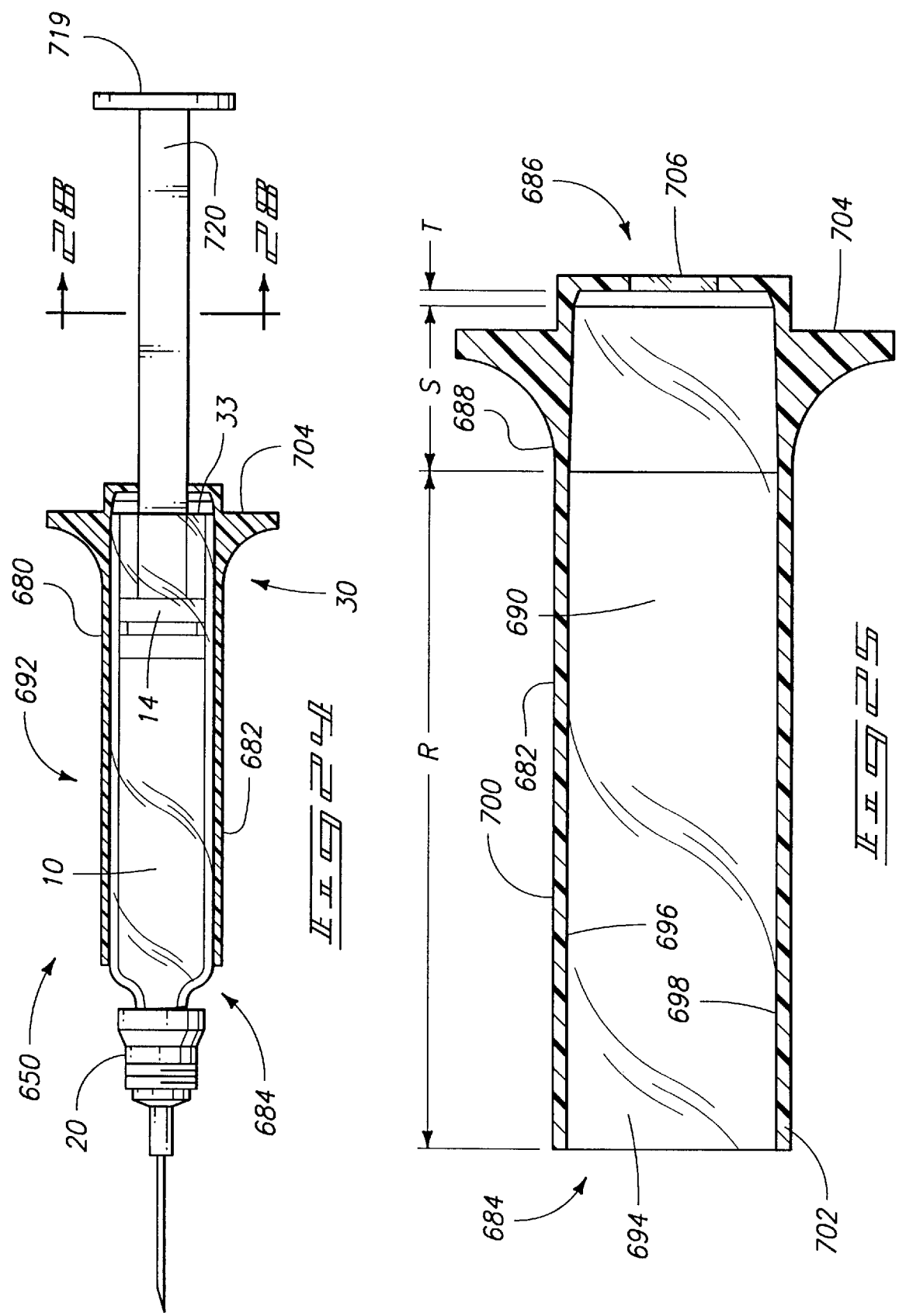

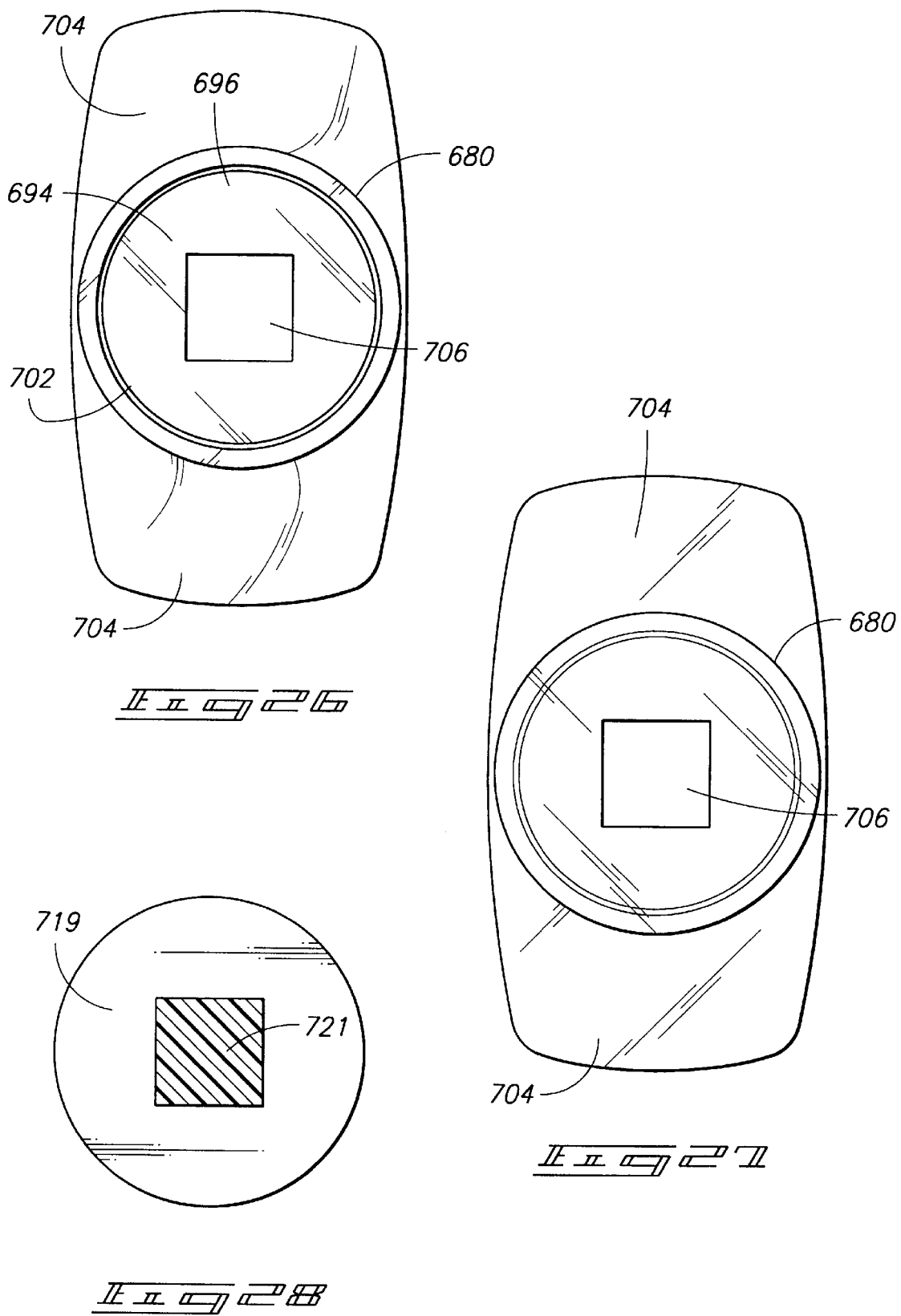

MEDICINE INJECTION SYRINGE CONSTRUCTIONS

CROSS-REFERENCE TO RELATED APPLICATIONS

This is a continuation-in-part of prior application Ser. No. 08/243,641, filed May 16, 1994 U.S. Pat. No. 5,540664. Prior application Ser. No. 08/243,641 was a continuation-in-part of Ser. No. 08/068,644, filed May 27, 1993 (now U.S. Pat. No. 5,358,489).

This is also a continuation-in-part of co-pending prior application Ser. No. 08/262,744, filed Jun. 20, 1994 abandoned.

TECHNICAL FIELD

This invention relates to injection devices for injecting medications into bodily tissue.

BACKGROUND OF THE INVENTION

Medicine injection syringe cartridges are known in the art. The cartridges consist of an ampule for housing and containing a fluid medication, a needle attached to the front of the ampule, and a plunger which is slidable within the ampule. The ampule is constructed such that force applied to the plunger causes the plunger to move and thus displace fluid medication from the ampule and through the needle. Examples of well-known prior art syringe cartridges are those sold under the brand names TUBEX by Wyeth Pharmaceuticals, and DOSETTE by Elkin-Sinn.

The prior syringe cartridges have been used with a number of different syringe cartridge holders. The prior syringe cartridge holders allow the syringe cartridge to be inserted into the holder and typically secured in position. The prior art syringe holders function to hold the syringe cartridge and allow manual or automatic displacement of the syringe cartridge plunger.

Some prior art syringe holders have been constructed to be used by medical professionals and can easily be used to administer varying dosages at the discretion of the medical professional. Such holders are not preferred where the holders are to be used by the patients or family and friends who may assist the patient at home to administer needed medication. To provide controlled dose administration it has been common to use relatively complex autoinjection devices which are costly to produce. This has been a deterrent to inexpensive distribution of injectable medications. Accordingly, it has been typical that many people who might otherwise be well-advised to carry or otherwise have injectable medications readily available have not in practice done so.

Prior art syringe cartridge holders have been relatively costly and have been reused with numerous injection cartridges. The prior art thus has provided a significant risk of accidental injury to nurses or physicians as they manipulate the syringe holder to remove the injection cartridge. The concern for such accidental injury has been great for many years, but more recently has been of increasing concern due to the larger numbers of people who carry the AIDS virus and other deadly communicable diseases. The long-felt need for an inexpensive, pre-filled disposable syringe has heretofore gone unsuccessfully answered.

Thus, a need has long existed for an inexpensive syringe injection cartridge holder easily used with existing syringe injection cartridges to provide a disposable syringe assembly, which can be provided with dose regulation for enhanced use by health care professionals, patients, or others.

BRIEF DESCRIPTION OF THE DRAWINGS

Preferred embodiments of the invention are described below with reference to the accompanying drawings, which are briefly described below.

FIG. 1 is a side view of a prior art medicine injection syringe cartridge.

FIG. 2 is a side view of a syringe cartridge such as shown in FIG. 1 converted using a first embodiment syringe cartridge converter and resulting syringe assembly according to the present invention.

FIG. 3 is a longitudinal sectional view of the assembly shown in FIG. 2.

FIG. 4 is an enlarged sectional view of a principle component of the syringe cartridge converter shown in FIG. 2, shown in isolation from remaining components of the syringe assembly.

FIG. 5 is a front or receiver-end view of the converter shown in FIG. 4.

FIG. 6 is a top view of the converter shown in FIG. 4.

FIG. 7 is a rear view of the converter shown in FIG. 4.

FIG. 8 is a longitudinal sectional view of an embodiment of the dosage regulating system of the present invention.

FIG. 9 is a cross-sectional view taken along line 9—9 of FIG. 8.

FIG. 10 shows an alternate plunger shaft and dose regulating construction which may be used in dosage regulating systems of the present invention.

FIG. 11 is an isometric view of an alternate embodiment of a removable dose regulating collar which may be used in the dosage regulating system of the present invention.

FIG. 14 is a side view of a further alternative embodiment syringe assembly according to the present invention. The assembly shown in FIG. 14 has a removable collar attached to an injection cartridge converter.

FIG. 15 is a longitudinal sectional view of a further syringe assembly according to another embodiment of the present invention.

FIG. 16 is an enlarged sectional view of a cartridge converter portion of the syringe assembly shown in FIG. 16.

FIG. 17 is a front or receiver-end view of the cartridge converter shown in FIG. 16.

FIG. 18 is a rear or shaft-end view of the cartridge converter shown in FIG. 17.

FIG. 19 is a longitudinal sectional view of a further syringe assembly embodiment constructed in accordance with the present invention.

FIG. 20 is an enlarged sectional view showing selected portions of the embodiment shown in FIG. 19.

FIG. 21 is a sectional view similar to FIG. 20 with the illustrated portions reconfigured to lock a syringe cartridge into position.

FIG. 24 is a longitudinal sectional view of a still further syringe assembly according to this invention.

FIG. 25 is an enlarged longitudinal sectional view of a selected body piece component forming part of the assembly shown in FIG. 24.

FIG. 26 is a front or receiver-end view of the component shown in FIG. 25.

FIG. 27 is a rear or shaft-end view of the component shown in FIG. 25.

FIG. 28 is a cross-sectional view taken along line 28—28 of FIG. 25.

DETAILED DESCRIPTION OF THE PREFERRED EMBODIMENTS

Figure 12:
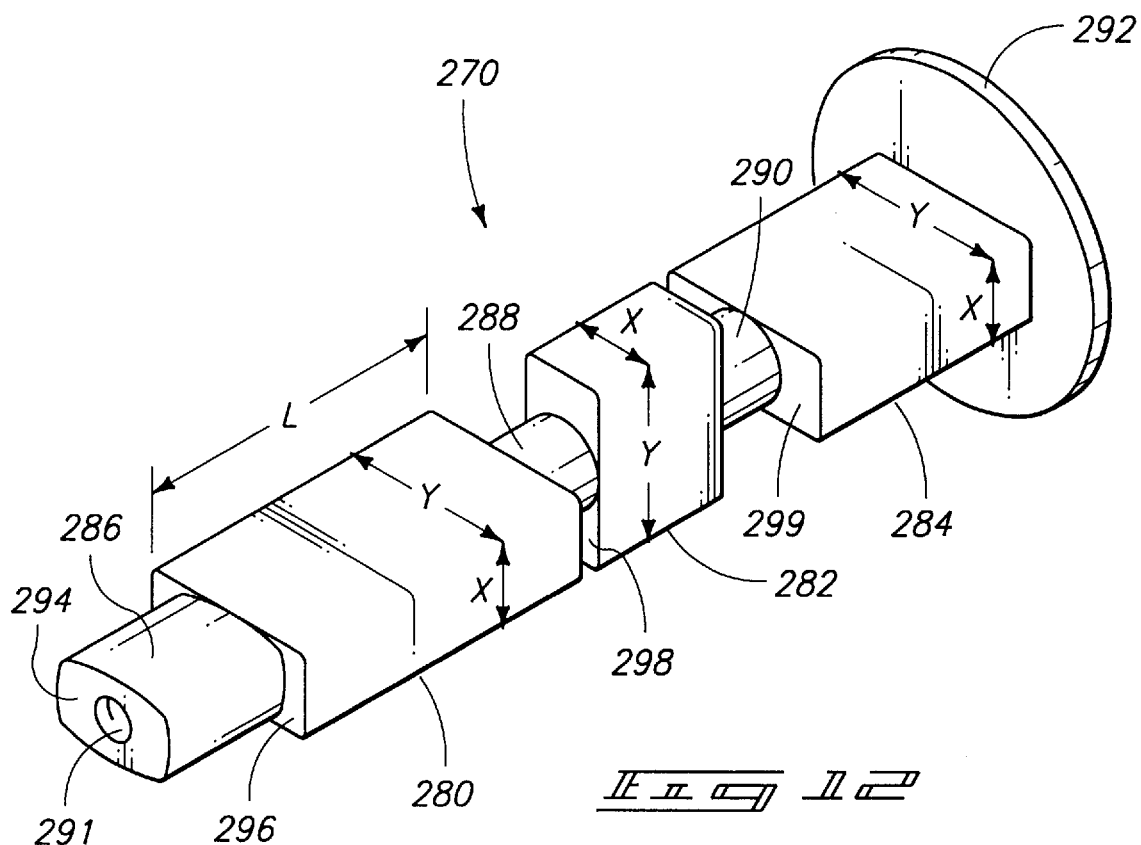
FIG. 12 is a perspective view of an alternative dosage regulating plunger shaft construction which can be used in the present invention.

This disclosure of the invention is submitted in furtherance of the constitutional purposes of the U.S. Patent Laws "to promote the progress of science and useful arts" (Article 1, Section 8).

TABLE 1

Listing of Subsections of Descriptions with Pertinent Items by Reference Number and Page Number

| | | |
|---|---|---|
| A. | Prior Art Syringe Cartridge | 8 |
| | medicine injection cartridge 10 | 8 |
| | ampule 12 | 8 |
| | fluid medication 18 | 8 |
| | nosepiece 20 | 8 |
| | needle 24 | 8 |
| | threaded engagement 22 | 8 |
| | needle cover or housing 26 | 8 |
| | plunger 14 | 8 |
| | stopper 15 | 8 |
| | plunger shaft connector 16 | 8 |
| | plunger shaft engagement end 30 | 9 |
| | needle end 32 | 9 |
| | shaft-receiving inlet 33 | 9 |
| B. | Embodiments of FIGS. 2–7 | 9 |
| | syringe assembly 50 | 9 |
| | injection cartridge converter 80 | 9 |
| | medicine injection cartridge 10 | 9 |
| B.1 | Injection Cartridge Converter | 9 |
| | converter body piece 82 | 9 |
| | engagement end 84 | 9 |
| | outward end 86 | 9 |
| | front or proximal end 84 | 9 |
| | rear or distal end 86 | 10 |
| | longitudinal axis 87 | 10 |
| | cartridge receiver 88 | 10 |
| | receiver sidewalls 102 | 10 |
| | inwardly facing surfaces 989 | 10 |
| | receiver receptacle 90 | 10 |
| | receptacle mouth opening 94 | 10 |
| | receptacle periphery 96 | 10 |
| | outer surfaces 100 | 10 |
| | gripping members 104 | 13 |
| | plunger shaft aperture 106 | 14 |
| | plunger shaft inlet 33 | 14 |
| | plunger shaft 120 | 14 |
| | distal end wall advantageously in the form of a cap 107 | 14 |
| | distal or outer surface 105 | 14 |
| B.2 | Converter Plunger Shaft | 14 |
| | plunger shaft end 205 | 14 |
| | engagement receptacle 123 | 14 |
| | shaft retainers 122 | 15 |
| C. | Dosage Regulator | 15 |
| | dosage regulating system 200 | 15 |
| | plunger shaft 120 | 15 |
| | fluid medication 18 | 15 |
| | needle 24 | 15 |
| | collars 204 | 15 |
| | stop 210 | 16 |
| | plunger head 205 | 16 |
| | first limit or collar 206 | 16 |
| | second limit or collar 208 | 16 |
| | breakable connection 209 | 16 |

TABLE 1-continued

Listing of Subsections of Descriptions with Pertinent Items by Reference Number and Page Number

| | | |
|---|---|---|
| | guide slots 220 | 16 |
| | slot engaging extensions 222 | 16 |
| | shaft embodiment 121 | 16 |
| | collar embodiment 211 | 16 |
| | tear-away removable collar 213 | 16 |
| | breakable detachable connection 209 | 18 |
| | tab 207 | 18 |
| | longitudinal break or slit 252 | 18 |
| | breakable septum or seam 256 | 19 |
| | outer edges 260 | 19 |
| | dose limit collar 213 | 19 |
| | pull tab 258 | 19 |
| | detachable web or septum 256 | 19 |
| | plunger shaft 270 | 19 |
| | engagement receptacle 291 | 19 |
| | non-removable limit blocks 280, 282 and 284 | 20 |
| | space regions 286, 288 and 290 | 20 |
| | shaft head 292 | 20 |
| | guide and stop piece 300 | 20 |
| | converter 80 | 20 |
| | aperture 106 | 20 |
| | body piece 302 | 20 |
| | rectangular aperture 304 | 20 |
| | indented regions 306 | 20 |
| | outer raised region 310 | 20 |
| | triangular shaped dogs 308 | 20 |
| | forward end 294 | 22 |
| | forward end 296 | 22 |
| | forward end 298 | 22 |
| | forward end 299 | 22 |
| D. | Embodiment of FIG. 14 | 24 |
| | syringe assembly 350 | 24 |
| | syringe body 352 | 24 |
| | shaft end 354 | 24 |
| | needle end 356 | 24 |
| | shaft 358 | 24 |
| | Dosage regulating system 360 | 24 |
| | removable collar 362 | 24 |
| | plunger shaft head 364 | 24 |
| | distal end 363 | 24 |
| | medication 353 | 24 |
| | needle 357 | 24 |
| | pull tab 370 | 24 |
| | longitudinal breakaway section 372 | 24 |
| E. | Embodiments of FIGS. 15–18 | 26 |
| | syringe assembly 400 | 26 |
| | medicine injection cartridge 10 | 26 |
| | injection cartridge converter 420 | 26 |
| | plunger shaft 446 | 26 |
| | dosage regulating system 411 | 26 |
| | body piece 422 | 26 |
| | proximal end 424 | 26 |
| | distal end 424 | 26 |
| | syringe body assembly 421 | 26 |
| | receiver receptacle 430 | 26 |
| | engagement end 424 | 26 |
| | receptacle opening 432 | 26 |
| | receptacle periphery 434 | 26 |
| | inwardly facing surfaces 436 | 26 |
| | self-locking receiver 428 | 26 |
| | ring projection 445 | 27 |
| | wall 429 | 27 |
| | gripping members 442 | 27 |
| | shaft-receiving aperture 444 | 28 |
| | cap 443 | 28 |
| | top outer surface 441 | 29 |
| F. | Embodiments of FIGS. 19–23 | 29 |
| | syringe assembly 500 | 29 |
| | medicine injection cartridge 10 | 29 |
| | plunger shaft 580 | 29 |
| | injection cartridge converter 520 | 29 |
| | dosage regulating system 579 | 29 |
| | syringe body assembly 521 | 29 |
| | body piece 522 | 29 |
| | Receiver 528 | 30 |
| | receptacle 530 | 30 |

TABLE 1-continued

Listing of Subsections of Descriptions with
Pertinent Items by Reference Number and Page Number

| | |
|---|---|
| receptacle opening i532 | 30 |
| receptacle periphery 534 | 30 |
| inwardly facing surfaces 536 | 30 |
| constrictive ring 537 | 30 |
| outer peripheral surface 546 | 30 |
| ridges 548 | 30 |
| locking flange 550 | 30 |
| compression surface 552 | 30 |
| collet or locking ring 560 | 30 |
| aperture 564 | 30 |
| internal surface 566 | 30 |
| walls 570 | 31 |
| shaft-receiving aperture 544 | 32 |
| G. Embodiment of FIGS. 24–28 | 33 |
| syring assembly 650 | 33 |
| medicine injection cartridge 10 | 33 |
| injection cartridge converter 680 | 33 |
| plunger shaft 720 | 33 |
| plunger shaft end 719 | 33 |
| square cross-sectional shape 721 | 33 |
| syringe body assembly 692 | 33 |
| body piece 682 | 33 |
| engagement end 684 | 33 |
| outward end 686 | 33 |
| proximal end 684 | 33 |
| distal end 686 | 33 |
| self-locking receiver 688 | 33 |
| receiver receptacle 690 | 33 |
| receptacle periphery 696 | 34 |
| inwardly facing surfaces 698 | 34 |
| outer peripheral surface 700 | 34 |
| regions R, S, and T | 35 |
| side wall 702 | 36 |
| gripping members 704 | 36 |
| aperture 706 | 37 |
| H. Methods for Assembly of Syringes | 38 |

A. Prior Art Syringe Cartridge

FIG. 1 shows a representative example of a medicine injection cartridge 10 currently available on the market. Cartridges having a construction similar to cartridge 10 are manufactured under the trademark TUBEX by Wyeth Laboratories, Inc., and under the trademark DOSETTE by Elkin-Sinn. Cartridge 10 comprises an ampule 12. Ampule 12 is preferably a glass or plastic vial that contains a measured amount of fluid medication 18. The amount of medication (such as antidotal medicant, antibiotics, epinephrine, insulin, etc.) varies depending upon the medication and anticipated usage conditions. Cartridge 10 includes a nosepiece 20 and a needle 24 attached to the nosepiece. In the illustrated embodiment, nosepiece 20 includes a threaded engagement 22 which can be used in alternative mountings. The nosepiece supports a removable needle cover or housing 26. Removable needle housing 26 is provided for safety purposes and covers needle 24 when injection cartridge 10 is not in use.

Cartridge 10 further includes a fluid-tight plunger 14 for forcing fluid medication 18 through a lumen (not shown) formed through needle 24. Plunger 14 includes a stopper 15 which engages and slides within ampule 12 in fluid sealed relationship. Stopper 15 is preferably formed of rubber or other suitable elastomeric material. Plunger 14 also has a plunger shaft connector 16 which faces outwardly. As shown, plunger shaft connector 16 is a threaded extension.

Injection cartridge 10 can be thought of as having two ends, a plunger shaft engagement end 30, also referred to as a rear end or distal end, and a needle end 32 which is also referred to as a fore end or proximal end. Injection cartridge 10 further comprises a shaft-receiving inlet 33 (shown in FIG. 3) in the plunger end 30 through which a plunger shaft may be inserted and engaged with plunger shaft receiver 16.

B. Embodiments of FIGS. 2–7

FIGS. 2–7 show a preferred syringe assembly 50 according to the invention. Syringe assembly 50 includes an injection cartridge converter 80 made according to the invention. Converter 80 is used with a medicine injection cartridge 10 to form the resulting syringe assembly 50. Injection cartridge 10 is as described above.

B.1 Injection Cartridge Converter

Converter 80 includes a converter body piece 82. As shown, converter body 82 is a unitary piece of suitable plastic material machined, molded or otherwise formed in the indicated shape to provide the desired features. Polycarbonate has in particular been found suitable for use in constructing converter body piece 82.

Converter body piece 82 which has an engagement end 84 and an outward end 86. Engagement end 84 and outward end 86 may alternatively be referred to as front or proximal end 84 and rear or distal end 86. A longitudinal axis 87 extends from proximal end 84 to distal end 86.

Converter 80 also includes a cartridge receiver 88 formed in body piece 82. Receiver 88 has receiver sidewalls 102 which advantageously extend in an annular configuration about the longitudinal axis 87. Sidewalls 102 have inwardly facing surfaces 98 which form a receiver receptacle 90. Receptacle 90 has a receptacle mouth opening 94 at the proximal end 84 of converter 80. Sidewalls 102 further form a receptacle periphery 96. Receiver 88 further includes outer surfaces 100.

Receiver 88 is configured such that cartridge 10 will be tightly secured within receptacle 90 when plunger end 30 of cartridge 10 is inserted into the receptacle. Thus, receptacle 90 is configured such that plunger end 30 of cartridge 10 can be wedged tightly against inwardly facing surfaces 98 of the receptacle. This configuration may be accomplished by forming at least one constriction along inwardly facing surfaces 98 of receiver receptacle 90. The at least one constriction is sized to allow insertion of plunger end 30 into receptacle 90 and is further sized so that the outer surfaces of injection cartridge 10 are engaged by inner surfaces 98 of receptacle 90. The interaction between the surfaces of injection cartridge 10 and the surfaces of receptacle 90 effectively develops forces between cartridge 10 and the at least one constriction so that mere insertion of plunger end 30 into receptacle 90 provides a self-locking action between cartridge 10 and body piece 82 when cartridge 10 is inserted into receiver 88.

The inwardly facing surfaces of receptacle 90 are preferably configured so as to converge advancing into the receptacle. The converging inward surfaces are preferably such that each inside surface tapers approximately a similar amount. The converging inward surfaces are advantageously conical. Alternatively, the converging surfaces can be formed along the inward surfaces of longitudinal ridges (not shown) or other suitable surface features which cover a portion of the inward surfaces. The converging inward surfaces are configured such that plunger end 30 of the cartridge can be wedged tightly into the receptacle. Receptacle 90 has a transverse cross-sectional area which decreases advancing into the receptacle, from the front toward the rear of the converter body piece. Receptacle 90 preferably tapers or otherwise converges at a convergence angle of less than approximately 5° of arc. As shown, the convergence angle is determined by approximately symmetrical conical surfaces and thus is equal to twice the taper angle associated with the taper of the inwardly facing surfaces 98. The taper angle is measured relative to longitudinal axis 87. More preferably, the convergence angle is less than approximately 2° of arc, even more preferably in the approximate range of 0.05°–1° of arc.

Alternatively, receptacle 90 may have a varying convergence or other general diminution in cross-sectional size. In one alternative form the receptacles comprises increasing convergence advancing into the receptacle. For example, two or more distinct regions can be provided, wherein each region is longitudinally displaced relative to the other regions and wherein at least two of the two or more regions have differing degrees of taper. Preferably, the tapers will be such that the general trend in cross-sectional size of receptacle 90 decreases advancing into the receptacle. Most preferably, a region with a greater degree of taper will be distal to one or more regions with a lesser degree of taper. In such an embodiment, the receptacle mouth 94 will be large enough to allow entry of the plunger end 30 of the injection cartridge. The distal end of the tapered receptacle will have an effective cross-sectional area less than the cross-sectional area of plunger end 30. Thus, when the cartridge plunger end is inserted into receptacle 90, there will be a portion of a tapered region which will firmly grasp plunger end 30. The relatively small amount of taper causes the cartridge to still be stabilized laterally near the mouth of the receptacle.

Another aspect of converter 80 is that side wall 102 is formed from appropriate material and of suitable thickness so that the wall will be slightly distorted when plunger end 30 is firmly engaged within receptacle 90. This enhances the ability of receiver 88 to grip and thereby self-lock onto cartridge 10. The relatively small taper or convergence angle provides an effective wedging action with great mechanical advantage which develops significant stress against the side wall. This stress causes the distortion which enhances the frictional grip of the cartridge within the receptacle and makes for a surprising amount of resistance against removal of the converter body 82 from the engagement end of ampule 12.

In a preferred form, the receiver side wall 102 is constructed of polycarbonate plastic and the following preferred wall thickness are believed appropriate. The side wall 102 is preferably less than approximately 0.1 inch thick, more preferably less than 0.05 inch thick, even more preferably less than 0.03 inch thick. Thickness of the side wall is most preferably to be in the range of approximately 0.01–0.03 inch. The preferred ranges provide wall thickness with this type of material which will respond to the force applied by hand to produce augmenting resistance to cartridge removal from the receptacle.

Converter body 82 also advantageously includes one or more grips in the form of gripping members 104 which extend from outer peripheral surface 100 of receiver 88. The gripping members are provided to improve the ease of handling and use of syringe assembly 50. Thus, gripping members 104 are configured to act as flanges which resist longitudinal displacement when engaged by one or more fingers of a human hand. The fingers are typically placed forward of the gripping members. As shown, gripping members 104 comprise a pair of ears, wherein each ear extends outwardly from receiver 88 and has a length of outward extension beyond the outer surfaces 100 which is range of approximately in the range of approximately 0.1–1 inch. The ears encourage a user to use the thumb and middle finger of a hand to hold the syringe and to press the plunger with the forefinger of the same hand.

Converter 80 further comprises an plunger shaft aperture 106 in outward end 86. Aperture 106 opens into receptacle 90 and forms a continuous passageway with a plunger shaft inlet 33 formed in plunger end 30 of the cartridge. Aperture 106 is configured to enable insertion of plunger shaft 120 therethrough so that the plunger shaft may be connected to plunger 14 using connector 16.

FIG. 7 shows that converter 80 also preferably comprises a distal end wall advantageously in the form of a cap 107 surrounding aperture 106 and substantially closing the end of receptacle 90. Cap 107 consists of the portion of receiver 88 which extends distally of gripping members 104. Cap 107 forms part of a distal or outer surface 105 of converter 80. The end wall can extend from the gripping members or be flush along the outer distal surface thereof.

B.2 Converter Plunger Shaft

Syringe assembly 50 further comprises a plunger shaft 120. Plunger shaft 120 can be provided as a separate element or as part of the converter 80. FIG. 3 shows that shaft 120 is preferably provided as part of a plunger shaft assembly which includes the shaft 120 and a plunger shaft end 205.

Plunger shaft 120 includes an engagement receptacle 123 (shown in FIG. 8). Engagement receptacle 123 is threaded for engaging the shaft to threaded connection stud 16 (shown in FIG. 1).

Plunger shaft 120 is preferably provided with shaft retainers 122. Shaft retainers 122 are advantageously in the form of small nub, ridge or other protuberance formed on the shaft. The nubs are sufficiently small to allow insertion into aperture 106 by simply forcing the shaft thereinto. Nubs 122 keep the shaft from falling out before the converter is installed and the plunger shaft is screwed onto connector 16.

The plunger shaft assembly shown in FIGS. 2 and 3 has been modified by incorporation of a dose regulating system 200 which is described in greater detail below.

C. Dosage Regulator

FIGS. 2, 3 and 8–14 illustrate a preferred dosage regulating system 200 according to the invention. FIG. 2 shows syringe assembly 50 that has been configured with the dosage regulating system of this invention. Dose regulator 200 is preferably provided as part of the converter assembly 80. Dose regulator 200 advantageously functions upon the plunger shaft 120. In the syringe assembly, plunger shaft 120 is connected to plunger 14, both being slidably engaged with other portions of syringe body 92. Inward movement of the plunger shaft will dispense fluid medication 18 from the syringe assembly through needle 24 (shown in FIG. 3).

Dosage regulating system 200 comprises one or more collars 204. Collars 204 act as detachable mechanical limits which serve to better define starting and ending positions for plunger 14. Dose regulator 200 also preferably includes at least one stop 210 formed upon converter body 82 against which limiting collar 204 bears when the plunger has been depressed. Regulator 200 also utilizes plunger head 205 which applies force against collars 204 in response to force applied manually by the user's finger against the outer surface of head 205.

FIG. 2 shows two collars 204 which are individually labeled as first limit or collar 206 and second limit or collar 208. As shown, collar 208 is attached to the head 205 of plunger shaft 120 with a breakable connection 209. Collar 206 is slidably engaged to shaft 120. This slidable engagement is illustrated in more detail in FIGS. 8 through 10. Shaft 120 is advantageously adapted to prevent collar rotation by including one or more guide slots 220 extending as needed along its length. Collar 206 includes one or more complementary slot engaging extensions 222. The combination of slots 220 and slot engaging extensions 222 enables collar 206 to slide up and down on shaft 120 but which restricts any twisting movement of the collar. The desirability of this restriction against twisting movement of the collars will become clearer when removal of the collar is discussed below.

FIG. 10 shows an alternative shaft embodiment 121 which comprises three guide slots 220, and a collar embodiment 211 which comprises three slot engaging extensions 222. FIG. 11 illustrates that the slot engaging extensions are not absolutely required and shows an alternative embodiment of tear-away removable collar 213 which as shown does not include anti-rotation features. Alternatively, collar 213 can be provided with such features.

In operation stop 210 is connected to syringe body 92 and collar 206 is engaged to shaft 120. Inward motion of plunger shaft 120 will eventually bring collar 206 into motion-impeding contact with stop 210. Plunger end 205 and collar 208 will be pushed firmly against collar 206 which in turn will be firmly abutted against stop 210. Thus, the interaction of collar 206 and stop 210 will impede further inward motion of the plunger shaft. This first stop position is used with the syringe oriented needle up so that any gases within ampule 12 are expelled along with excess fluid medication. This sets the plunger at a starting position which is predefined relative to additional positions defined by the dose regulator as will be explained more below.

The length A of plunger shaft 120, length B of collar 206 and length C of collar 208 are calibrated so that motion-impeding contact between stop 210 and collar 206 occurs after a predetermined displacement has occurred which is sufficient to assure displacement of all gas and an initial wastage of medicine. This amount is sufficient for a range of ampule fill levels which varies due to production variations associated with injection cartridge 10. Lengths A, B, and C will also vary dependent upon the type of cartridge, type of medicine and prescribed dose to be used.

Although dosage regulating system 200 is a two-collar system designed for dispensing two predetermined doses of medicine from a single injection cartridge, the system could easily be adapted to a single collar system for injection of a single measured dose of medication or adapted to provide more than two collars for dispensing more than two predetermined doses of medication from a single injection cartridge.

Referring now to the specific collar design shown in FIGS. 2 and 8–14, it is to be understood that the collars or other dose limits can take on a number of shapes and configurations. The collars are configured such that they can come into motion-impeding contact with a stop to thereby impede inward motion of a syringe plunger shaft. Also, the collars should preferably be considered such that the motion-impeding contact can subsequently be eliminated thereby allowing motion of the plunger shaft to continue such that a predetermined measured dose of medication is dispensed from a syringe that is attached to the plunger shaft. Also preferably, the dosage of medication dispensed will be proportional to the length of the collars.

Collar limits 206 and 208 are preferably adapted to be removable. Collar 208 is attached to the head 205 of plunger shaft 120 with a breakable detachable connection 209. Breakable connection 209 preferably has a tab 207 to facilitate breaking the connection 209. Collar 208 further comprises a longitudinal break or slit 252 which extends along the length of collar 208. Collar 208 is preferably formed of a relatively flexible material so that once connection 209 is broken, collar 208 can be readily opened along slit 252 and released from plunger shaft 120.

Collar 206 incorporates an alternative construction which provides a different way of removing the collar as compared to collar 208 described above. Collar 206 includes a breakable septum or seam 256 which extends along its length. Collar 206 and breakable seam 256 are preferably constructed such that seam 256 can be broken to form a slit or discontinuity which divides the complementary edges of the collar. Collar 206 can be ruptured simply by pushing inwardly on outer edges 260 of collar 206. Collar 206 can be broken and then manually grasped and opened like a clamshell to remove it shaft 120. Restriction of the twisting motion of collar 206 about shaft 120 is advantageous in that such restriction makes it easier for a person to grasp collar 206 and break seam 256.

FIG. 11 shows and alternative dose limit collar 213 which can be used in lieu of collar 206. Collar 213 includes a pull tab 258 which is connected to a detachable web or septum 256. Tab 258 provides a grasp and simplifies the removal of septum 256 by a human hand. Most preferably, breakable septum 256 will be composed of plastic which can be torn away longitudinally without undue force. Alternatively, septum 256 can be replaced by a pre-formed split and no breakage is needed to remove the collar.

Figure 13:
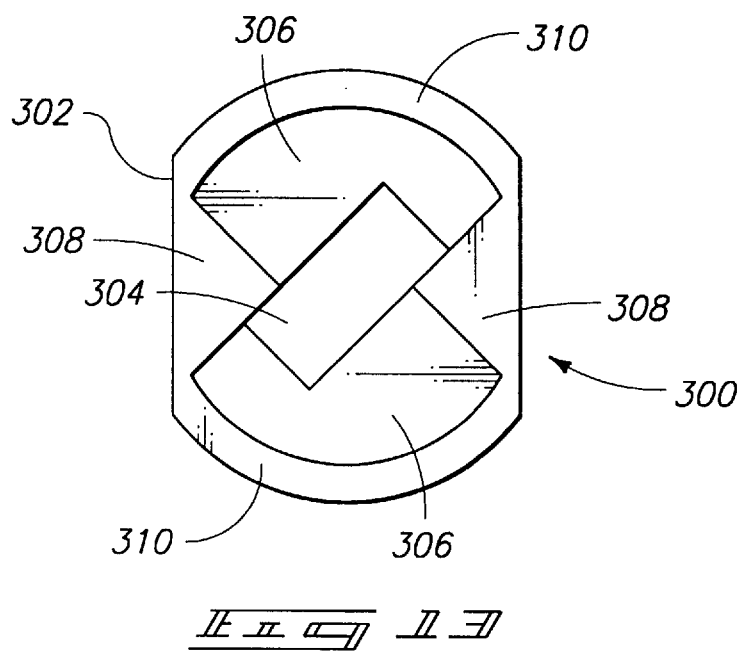
FIG. 13 is an end view of the plunger shaft construction shown in FIG. 12.
Figure 22:
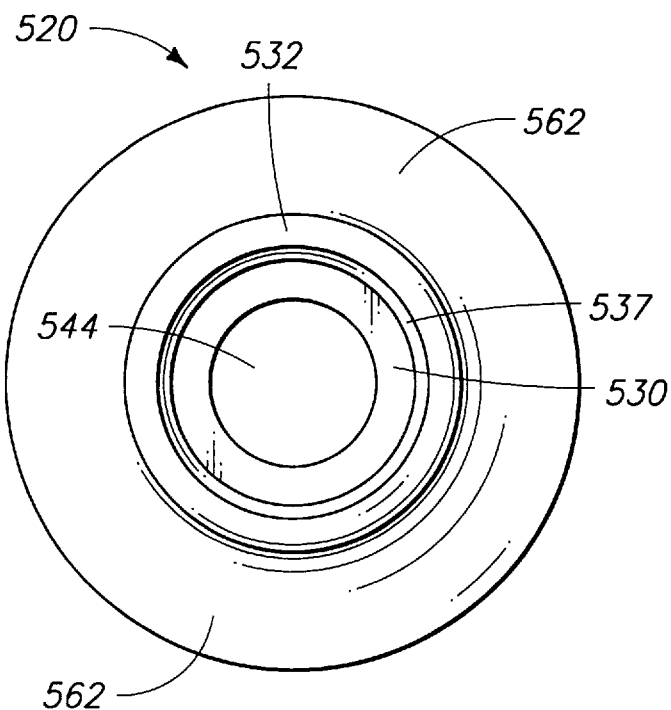
FIG. 22 is a front or receiver-end view of selected portions similar to those shown in FIG. 20.
Figure 23:
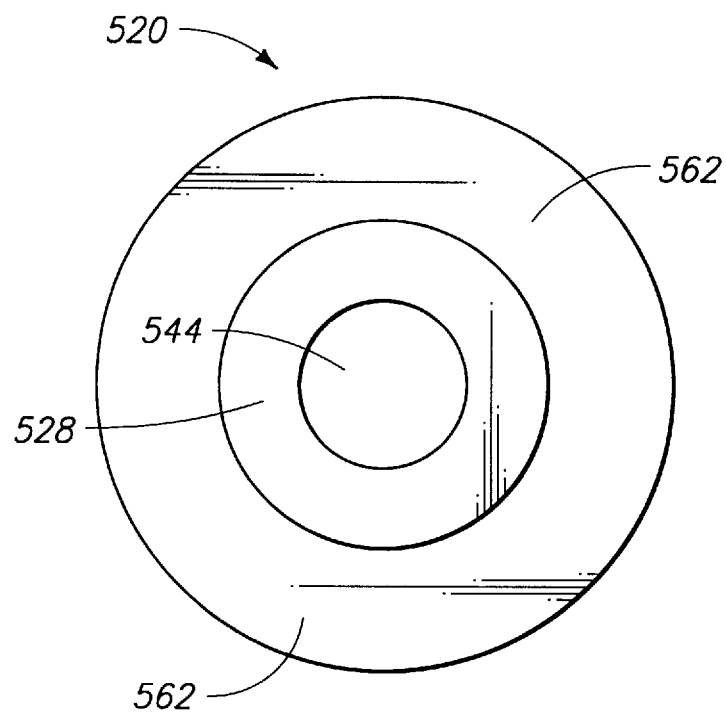
FIG. 23 is a rear or shaft-end view of selected portions similar to those shown in FIG. 20.

FIGS. 12 and 13 show a further alternative dose regulator construction which can be used in the converters and syringe assemblies made in accordance with the invention. FIG. 12 shows generally a plunger shaft 270 comprising an engagement receptacle 291 for engaging the plunger connector 16 (see FIG. 1). Shaft 270 is provided with a series of non-removable limit blocks 280, 282 and 284. Limit blocks 280, 282 and 284 preferably have somewhat rounded corners to ease operation. Shaft 270 further includes intervening spacer regions 286, 288 and 290 which are preferably cylindrical. Shaft 270 has a shaft head 292.

Shaft 270 is designed to interact with a guide and stop piece 300 shown in FIG. 13. Guide and stop piece 300 receives shaft 270 therethrough to form a plunger shaft guide mechanism which provides dosage regulating functions. In practice, guide 300 can be attached to a cartridge converter, such as converter 80 shown in FIG. 7 so that guide 300 covers or forms aperture 106 of the converter. Alternatively, guide 300 can be used with a suitable syringe assembly simply by placing guide 300 over the plunger shaft receiving inlet of the syringe body and by using a plunger shaft 270 which can progress through guide 300 in selected orientations.

Referring to FIG. 13, guide 300 consists of a body piece 302 which includes a generally rectangular aperture 304. Aperture 304 is sized to allow limit blocks 280, 282 and 284 to pass therethrough when the blocks are oriented in the proper angular orientation. Adjacent to aperture 304 are indented regions 306 and outer raised region 310. Portions of the outer raised region form triangular shaped dogs 308 which limit rotation of the shaft 270 to approximately one-half turn.

The dimensions of aperture 304 are such that limit blocks 280, 282 and 284 can slide through aperture 304 in a first orientation but cannot otherwise slide through aperture 304. Limit blocks 280, 282 and 284 will all have the same dimensions of width Y and depth X but may vary in the dimension of length L. If block 280 is correctly oriented to slide through aperture 304, then block 282 will necessarily be incorrectly oriented to slide through aperture 304. Accordingly, if block 280 is aligned with aperture 304 and then shaft 270 is pushed downwardly into aperture 304, eventually the downward motion of shaft 280 will be impeded as block 282 comes into contact with a stop surface formed by indented areas 306. Second limit block 282 can then be rotated about 90° because the intervening spacer section 288 can turn within aperture 304. The length of the spacer section is slightly longer than the thickness of piece 302 adjacent to recessed areas 306. The downward progress of shaft 270 can continue after the shaft is reoriented. Again the downward progress of the shaft will be impeded as third limit block 284 comes into contact with guide 300. Again shaft 270 can be rotated 90° when cylindrical spacer section 290 is adjacent piece 302. Then the inward progress of the shaft can continue until head 292 abuts piece 302.

Preferably, guide 300 and shaft 270 will be constructed such that plunger shaft receptacle 291 of shaft 270 can be inserted into aperture 304 and twisted onto the threaded plunger shaft connector 16. Thus, shaft 270 includes a spacer 286 of sufficient length that plunger shaft receptacle 290 can be threaded onto connector 16. Also, it will be noted that shaft 270 has a forward end 294, first limit block 280 has a forward end 296, second limit block 282 has a forward end 298, and third limit block 284 has a forward end 299.

In one aspect of the invention, guide 300 is mounted over the shaft engagement end of a syringe body assembly, such as syringe body assembly 92 in FIG. 2, and shaft 270 is inserted through rectangular aperture 304. Preferably, the distance from forward end of shaft 294 to forward end of block 298 will be such that when block 280 is in aligned orientation with aperture 304 and pushed downward into cartridge 10 of the syringe body assembly, gas within ampule 12 will be expelled from the needle by the time that forward end 298 serves as a first limit which makes a motion-impeding contact with guide 300. The motion-impeding contact between forward end 298 and guide 300 is herein referred to a first motion-impeding contact generated by inward motion of plunger shaft 270.

After the first motion-impeding contact, forward end 298 will rest on indented region 306, and spacer 288 will be within aperture 304. Shaft 270 can then be rotated 90° so that block 282 is oriented with rectangular aperture 304 and can then be inserted into aperture 304. Dogs 308 prevent shaft 270 from being rotated more than 90°, and thus aid in orienting block 282 with rectangular aperture 304.

As block 282 is inserted in aperture 304, forward end 299 can be thought of as a second limit. The inward motion of shaft 270 will eventually be halted due to a motion-impeding contact between forward end 299 and guide 300. This motion-impeding contact is referred to herein as a second motion-impeding contact. Preferably, the length from forward end 298 to forward end 299 will be calibrated to correspond to a predetermined dose of medication that is to be dispensed from injection cartridge 10. Thus, preferably a predetermined dose of medication will be forced out of cartridge 10 as a result of the inward progression of shaft 270 between the first motion-impeding contact and the second motion-impeding contact.

After the second motion-impeding contact, front edge 299 will rest on indented region 306 and spacer 290 will be within aperture 304. Shaft 270 can then be rotated 90° in order to orient rectangular collar 284 with rectangular aperture 304. The shaft can then be inserted further through stop 300 and into the syringe body assembly. As collar 284 is inserted in aperture 304, plunger end 292 can be thought of as a third limit. The downward motion of shaft 270 will eventually be halted due to a motion-impeding contact between guide 300 and plunger end 292. This motion-impeding contact is referred to herein as a third motion-impeding contact. Preferably the distance from front edge 299 to plunger end 292 will be calibrated so that when block 284 is pushed downwardly into stop 300, a predetermined dose of medication will be dispensed from cartridge 10 in syringe body assembly 92.

Thus, a person can use a syringe adapted with shaft 270 and guide 300 to administer two predetermined doses of medication from a syringe body assembly. The first dose of medication is injected when second block 282 is pushed through aperture 304, and the second dose of medication is injected when third block 284 is pushed through aperture 304. Shaft 270 can be modified to have additional or fewer limit blocks to provide additional or fewer doses.

D. Embodiment of FIG. 14

FIG. 14 shows another embodiment of a dosage regulating system according to this invention. FIG. 14 shows syringe assembly 350 comprising a syringe body 352 which has a shaft end 354 and a needle end 356. Syringe body 352 is formed by assembly of a syringe injection cartridge 10 with a converter body similar to 80 described above. Syringe assembly 350 further comprises a shaft 358 slidably engaged within shaft end 354 of body 352. Dosage regulating system 360 includes a removable collar 362. Collar 362 is attached to shaft end 354 of syringe body 352. A plunger shaft head 364 forms a shaft travel limit which is co-extensive with distal end 363 of shaft 358. This embodiment of the dosage regulating system is configured to inject a single predetermined dose of medication 353 out of syringe body 352 and through needle 357. The initial space between the collar and shaft head allows for expelling gas and presetting the plunger to a starting reference point.

Collar 362 contains a pull tab 370 connected to a longitudinal breakaway section 372. Thus, when a person pulls on pull tab 370, the person will pull away the longitudinal breakaway section 372 and form a longitudinal opening within collar 362. Collar 362 is attached to distal end 354 with a breakaway type connection, such as a very thin plastic, so that once a longitudinal opening is formed in collar 362, collar 362 can easily be torn away from syringe 352 and released from around shaft 358.

The length of collar 362 and shaft 358 will be calibrated such that when shaft 358 is pushed inwardly into syringe body 352, motion-impeding contact will occur between collar 362 and limit 364 only after any gas contained within needle 357 has been expelled from the needle. The breakaway section is then removed by pulling upon tab 370. Collar 362 is then peeled from the shaft to allow full depression of the plunger.

The length of collar 362 will be calibrated such that when collar 362 is removed, a predetermined dose of medication will be dispensed from syringe 352 as shaft 358 is pushed downwardly into syringe 352 until limit 364 makes contact with distal end 363 of syringe body 352.

It is to be understood that any of the dosage regulating embodiments, or combinations of embodiments of the dosage regulating system discussed herein could be used with any of the embodiments or combinations of embodiments of cartridge converters discussed herein.

E. Embodiments of FIGS. 15–18

FIGS. 15 through 18 illustrate a further cartridge converter and syringe assembly according to this invention. Specifically, FIG. 15 shows a syringe assembly 400. Syringe assembly 400 comprises a medicine injection cartridge 10, and injection cartridge converter 420. Converter 420 includes a plunger shaft 446 and dosage regulating system 411. The plunger shaft 446 is similar to shaft 120 described above. Dose regulator 411 is similar to dose regulator 200 described above or other dose regulators described herein.

Attached to cartridge 10 is a cartridge converter 420. Converter 420 is shown as part of assembly 400 in FIG. 15 and is shown in isolation in FIGS. 16 through 18. Cartridge converter 420 comprises a body piece 422 which has a proximal end 424 and a distal end 426. Body piece 422 engages with the cartridge 10 to form a syringe body assembly 421. Cartridge converter 420 further comprises a receiver receptacle 430 which opens at engagement end 424 and which is configured for receiving and tightly securing plunger end 30 of injection cartridge 10. Receptacle 430 comprises a receptacle opening 432 at engagement end 424 of the receiver, and a receptacle periphery 434 formed within the receiver. Receptacle 430 further comprises inwardly facing surfaces 436 around receptacle periphery 434.

Receptacle 430 is part of a self-locking receiver 428 which is configured so that it may be slipped over plunger end 30 of cartridge 10 and tightly secure plunger end 30 within receptacle 430. The configuration for tightly securing plunger end 30 is at least one constriction formed along inwardly facing surfaces 436 of periphery 434. The at least one constriction being one or more inwardly directed projections, which as shown are in the form of a ring projection 445. Internal ring projection 445 is formed along inwardly facing surfaces 436. Ring 445 is sized and configured such that once plunger end 30 is inserted into the ring constriction 445, it becomes difficult for plunger end 30 to move from receptacle 430.

Another aspect of converter 420 is that receiver 428 comprises wall 429 around receptacle 430. Preferably, wall 429 is formed from distortable material so that wall 429 will be distorted when plunger end 30 is engaged within receptacle 430. This enhances the ability of receiver 428 to grip and thereby self-lock onto cartridge 10. Wall thickness described above also apply to this embodiment with measurements being aside from ring 445; however the most preferred range is expected to be larger, such as in the range 0.02–0.05 inch. This is due in part to the desire that this embodiment be made from more resilient plastics, rubber or other suitable materials.

As shown in FIGS. 15 through 18, converter 420 will preferably comprise one or more gripping members 442 which are formed on outer peripheral surface 438 of converter body 422. Gripping members 442 are configured for gripping by one or more fingers of a human hand so that syringe assembly 400 can be readily used. Preferably, gripping members 442 are formed so that the finger grips will be proximal in relation to ring 445. The proximal relation of the grips to ring 445 improves the slip-retarding capabilities of ring 445, particularly if converter 420 is formed of a compressible, relatively soft plastic material. The improvement in slip-retarding capabilities is caused by compression of gripping members 442 by a person's fingers during use of syringe assembly 400. Preferably, the compression of gripping members 442 is translated through the material of converter 420 to a compressive force at ring 445. The compressive force is then applied to increase the strength of the connection between ring 445 and plunger end 30 of cartridge 10. Accordingly, ring 445 is able to grip plunger end 30 more tightly and thus the slip-retarding capabilities of ring 445 are improved.

Although the slip-retarding ring is described as a separate embodiment of the invention, the slip-retarding ring could be used in conjunction with other embodiments of the invention.

Converter 420 further comprises a shaft-receiving aperture 444 in outward end 426. Aperture 444 opens into receptacle 430 and forms a continuous passageway with the receiving inlet 33 in plunger end 30. Aperture 444 is configured to enable insertion of plunger shaft 446 therethrough so that plunger shaft 446 may be connected to plunger 14. Also, as shown in FIG. 18, a preferred embodiment of the converter comprises a cap 443 surrounding aperture 444. Cap 443 consists of the portion of receiver 428 which extends distally of gripping members 442. Cap 443 forms part of a top outer surface 441 of converter 420.

Converter 420 is preferably formed from molded plastic or rubber and preferably consists of one integral piece. It is anticipated that manufacturers of cartridge 10 will be able to sell cartridge 10 and converter 420 as a syringe assembly kit, as preassembled syringe body assembly 421, or as a fully assembled syringe assembly, such as syringe assembly 400. The economical construction of converter 420 and other converters described herein provide a practical disposable syringe construction which will reduce the risks associated with giving injections to people or animals infected with blood transmissible diseases.

F. Embodiments of FIGS. 19–23

FIGS. 19–23 illustrate a still further form of injection cartridge converter according to this invention. FIG. 19 shows a syringe assembly 500 comprising a medicine injection cartridge 10, a plunger shaft 580, and an injection cartridge converter 520. Plunger shaft 580 forms part of a dosage regulating system 579. The general aspects of the dosage regulating system are described in detail above.

Attached to cartridge 10 is a converter 520 which converts cartridge 10 into a syringe body assembly 521. Converter 520 of assembly 500 is shown in FIG. 19 and in expanded views in FIGS. 20 through 23. Converter 520 comprises a body piece 522 which has a proximal end 524 and a distal end 526. Alternatively, proximal end 524 may be referred to as injection cartridge engagement end 524 and distal end 526 may be referred to as outward end 526. Body 522 further comprises a receiver 528 configured for receiving plunger end 30 of injection cartridge 10. Receiver 528 comprises a receptacle 530 within the receiver which has a receptacle opening 532 at proximal end 524. Receptacle opening 532 is configured to enable insertion of plunger end 30 into receptacle 530. Receptacle 530 further comprises a receptacle periphery 534 and inwardly facing surfaces 536 on said periphery. Preferably, receptacle 530 will also comprise a constrictive ring 537 formed along inwardly facing surfaces 536 with said ring being configured to tightly grasp plunger end 30 of cartridge 10 when cartridge 10 is inserted into receiver 528 and the entire cartridge converter 520 is fully assembled. The general features of slip-retarding constrictive ring 537 are discussed in more detail in the above discussion of the previous embodiment.

Returning now to discussion of receiver 528, the receiver comprises an outer peripheral surface 546 which includes one or more ridges 548. At least one of the one or more ridges 548 comprises a locking flange 550, and preferably at least one of the one or more ridges 548 will comprise a compression surface 552.

Receiver 528 is configured to work in conjunction with a second part of injection cartridge converter 520 which is referred to herein as collet or locking ring 560. Collet 560 includes an aperture 564 which has an internal surface 566 surrounding the aperture. Surface 566 is configured to slide over ridge 548 and lock onto locking flange 550. Aperture 564 is preferably sized so that when collet 560 is slid onto locking surface 550, a compressive force is generated which tightly secures receiver 528 against cartridge 10. Receiver 528 is preferably formed from an elastically compressible material so that when a compressive force is generated onto receiver 528, the receiver deforms to tightly secure cartridge 10.

As shown in FIGS. 19 through 21, receiver 528 comprises walls 570 which separate outer peripheral surface 546 from the peripheral surfaces 536 of the receptacle. Walls 570 have thicknesses as described above, or in the most preferred range of 0.02–0.08 inch so that they are appropriately deformable for optimum engagement of receiver 528 onto cartridge 10.

Also shown in FIGS. 19 through 21 is a collet holding or locking feature in the form of a ridge 554 present on the outer peripheral surface 546 of receiver 528.

Collet 560 is also advantageously used to provide a grip 562 which is configured for gripping by one or more fingers of a human hand. The grip aids in use of converter 520 when the converter is attached to a syringe assembly. The grip also aids in assembling the two-piece converter 520.

The assembly of converter 520 is shown by FIGS. 20 and 21. FIG. 20 shows the converter in a pre-assembled state in which collet 560 is at the proximal end of receiver 528 and has not yet been slid onto locking surfaces 550. FIG. 21 shows converter 520 after assembly. As the collet is fully installed, the inner surface 566, which is complementary to ridge 548, is slid over the ridge and locked onto locking surface 550.

Converter 520 further comprises a shaft-receiving aperture 544 in outward end 524. Aperture 544 opens into receptacle 530 and forms a continuous passageway with the receiving inlet 33 in plunger end 30. Aperture 544 is configured to enable insertion of plunger shaft 580 therethrough so that plunger shaft 580 may be connected to plunger 14.

Converter 520 is preferably formed from molded plastic or rubber. It is anticipated that manufacturers of cartridge 10 will be able to sell cartridge 10 and converter 520 as a syringe assembly kit, as a preassembled syringe body assembly 521, or as a fully assembled syringe assembly, such as syringe assembly 500.

Converter 520 is considered to be a preferred embodiment of the injection converter for applications in which relatively high pressure must be applied via a syringe assembly. In such applications, a person using a syringe assembly will exert considerable force on the grips of the converter. Since converter 520 has a separate force exerting piece, collet 560, which is compressively holding receiver 528 additional holding forces are applied to cartridge 10.

G. Embodiment of FIGS. 24–28

FIGS. 24–28 illustrates a further injection cartridge converter and syringe assembly according to the present invention. FIG. 24 shows a syringe assembly 650 comprising a medicine injection cartridge 10, an injection cartridge converter 680, and a plunger shaft 720. Plunger shaft 720 of assembly 650 comprises a plunger shaft end 719 and has square cross-sectional shape 721, as shown in FIG. 28. The square cross-sectional shape of plunger shaft 720 is shown merely to illustrate that alternate embodiments of plunger shaft construction can be incorporated into the embodiments of converters and the dosage regulating systems disclosed herein.

Attached to medicine injection cartridge 10 is an injection cartridge converter 680 which converts injection cartridge 10 into syringe body assembly 692. Converter 680 is shown as part of assembly 650 in FIG. 24 and is shown in isolation in FIGS. 24–27. Converter 680 comprises a body piece 682 which has an engagement end 684 and an outward end 686. Engagement end 684 and outward end 686 may alternatively be referred to as proximal end 684 and distal end 686, respectively.

Converter 680 further comprises a self-locking receiver 688 formed in body piece 682. Receiver 688 in turn comprises a receiver receptacle 690 which opens at receptacle opening 694 in proximal end 684 of converter 680. Receiver receptacle 690 further comprises a receptacle periphery 696 and inwardly facing surfaces 698 at the periphery 696. Receiver 688 further comprises an outer peripheral surface 700.

Receiver 688 is configured such that cartridge 10 will be tightly secured within receptacle 690 when plunger end 30 of cartridge 10 is inserted into the receptacle. Thus, receptacle 690 is configured such that plunger end 30 of cartridge 10 can be wedged tightly against inwardly facing surfaces 698 of the receptacle. Such a configuration is preferably accomplished by forming at least one constriction along inwardly facing surfaces 698 of receiver receptacle 690. The at least one constriction is sized to allow insertion of plunger end 30 into receptacle 690 and is further sized so that the outer surfaces of injection cartridge 10 are engaged by inner surfaces 698 of receptacle 690. The interaction between the surfaces of injection cartridge 10 and the surfaces of receptacle 690 develop forces between cartridge 10 and the at least one constriction so that mere insertion of plunger end 30 into receptacle 690 provides a self-locking action between cartridge 10 and body piece 682 when cartridge 10 is inserted into receiver 688. Receptacle 690 is shaped and configured such that plunger end 30 can be wedged tightly into the receptacle.

In the embodiment of the converter shown in FIGS. 24–27, receiver 688 comprises at least three receiver regions. Each region is longitudinally displaced relative to the other regions. Each of the three regions have differing degrees of convergence. Receiver 688 has a first region with a first convergence which is advantageously very low or effectively parallel. This allows the varying specific sizes of ampules to pass into the receptacle without applying undue force. Receiver 688 also has a second region with a second convergence that is greater than the first region convergence. A third region with a third degree of convergence which is greater than the second degree of convergence is also included. All three regions are oriented such that the general cross-sectional area of receptacle 690 decreases distally advancing into the receptacle.

The relative configuration of the cross-sectional area of receptacle 690 and of the tapers will be such that a proximal end of a tapered region will have a cross-sectional area greater than the cross-sectional area of plunger end 30, while a distal end of a tapered region will have a cross-sectional area less than the cross-sectional area of plunger end 30. Thus, when plunger end 30 is inserted into receptacle 690, there will be a portion of a tapered region which will firmly grasp plunger end 30. The three regions of converter 680 are shown in FIG. 25 as regions R, S and T. In the converter shown in FIG. 25, region R has a very slight degree of taper that is too slight to illustrate in FIGS. 25–27. Of course it is also possible to construct embodiments of the invention in which one or more of the three regions have no degree of taper. Such embodiments would generally be equivalent to either the first or second embodiments of the invention that are described above. The convergence used in the three or more sections will typically fall into the desired levels explained above. FIGS. 24 and 25 have exaggerated convergence tapers to more clearly illustrate the concept.

As shown in FIGS. 24 and 25, converter 680 is preferably quite long with respect to cartridge 10. The receptacle is made deep so that the side wall 702 extends along the ampule to provide effective protection against breakage or injury. In this embodiment converter 680 will be at least one-third of the length from the proximal end of nosepiece 20 to plunger end 30 of cartridge 10. More preferably, converter 680 will be at least one-half of the length from the proximal end of nosepiece 20 to plunger end 30 of cartridge 10, and most preferably converter 680 will be at least three-quarters of this length.

Another aspect of converter 680 is that receiver 688 comprises side wall 702 around receptacle 690. Preferably, wall 702 is formed from distortable material so that wall 702 will be distorted when plunger end 30 is engaged within receptacle 690. This enhances the ability of receiver 688 to grip and thereby self-lock onto cartridge 10. Most preferably, wall 702 will be elastically distortable and will have thicknesses as described above.

Another aspect of the invention is that one or more gripping members 704 may be attached to outer peripheral surface 700 of receiver 688. Preferably, the gripping surfaces will be attached near distal end 686 of converter 680. The gripping members are provided to improve the ease of use of syringe assembly 650. Thus, gripping members 704 are configured for gripping by one or more fingers of a human hand. Preferably, gripping members 704 comprise a pair of ears, wherein each ear extends outwardly from receiver 688 and has a length of outward extension which is as indicated above. The ears encourage a user to use the thumb and middle finger of a hand to hold the syringe and to press the plunger with the forefinger of the same hand.

Converter 680 further comprises an aperture 706 in outward end 686. Aperture 706 opens into receptacle 690 and forms a continuous passageway with the receiving inlet 33 in plunger end 30. Aperture 706 is configured to enable insertion of plunger shaft 720 therethrough so that plunger shaft 720 may be connected to plunger 14. Thus, since the plunger shaft embodiment incorporated into assembly 650 is a square shaft, aperture 706 is a square-shaped aperture. Alternatively, converter 680 is better constructed with a cylindrical shaft when assembled without dose control. The square shaft is used when dose control is included. Dose control has not been shown in FIG. 24 for simplicity.

It is noted that the shaft engagement of cartridge 10 that has been shown throughout this disclosure is a threaded engagement (see, e.g., engagement 22 in FIG. 1), and that the square shape of shaft 720 and aperture 706 could complicate a process of threadably engaging shaft 720 onto a shaft engagement. However, the cartridge is simply positioned with connector 16 against the mating part of the shaft and the cartridge is turned.

Converter 680 is preferably formed from molded plastic or rubber and preferably consists of one integral piece. It is anticipated that manufacturers of cartridge 10 will be able to sell cartridge 10 and converter 680 as a syringe assembly kit, as a preassembled syringe body assembly 692, or as a fully assembled syringe assembly, such as syringe assembly 650.

It is to be understood that converter 680 can be utilized with any of the combinations of plunger shaft constructions and dosage regulators disclosed herein and it is to be understood that any of the other converters disclosed herein could also be utilized with any of the combinations of plunger shaft constructions and dosage regulators disclosed herein. It is also to be understood that a large number of alternate shaft constructions which have not been specifically discussed in this disclosure could be utilized with the converters and dosage regulators of this invention.

H. Methods for Assembly of Syringes

The invention also includes novel methods for producing syringe assemblies. The novel syringe assemblies are preferably formed from injection cartridges, such as the widespread cartridges 10, using the novel converters. The preferred methods include selecting a suitable converter having a receiver with a receiver receptacle, such as those described above. The preferred receiver receptacles preferably have converging inwardly facing receptacle surfaces for engaging an injection cartridge to be inserted therein. The novel methods can further be selective with regard to other features of the converters disclosed above.

The methods also preferably include inserting a plunger end of the injection cartridge into the receiver receptacle. This inserting is preferably performed in a manner which further effects a wedging action with the cartridge ampule being wedged between surfaces of the receptacle. This wedging action produces relatively high normal forces between the ampule and the receptacle. These relatively high normal forces develop resistive frictional forces which prevent dislodgement of the cartridge from the receptacle.

The novel methods advantageously further include distorting sidewalls of the receiver to intensify resistive forces which keep the cartridge installed in the receptacle of the converters.

Methods of this invention still further preferably include compressing sidewalls of the receiver, such as by forcing the locking ring 560 against complementary surfaces which result in compressive forces being develop. The compressing step can additionally be served by locking the ring in position upon the receiver.

Methods according to this invention further advantageously include connecting the plunger shaft to the cartridge, such as at plunger connector 16.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A medicine injection syringe assembly, comprising:

an injection cartridge having an ampule in which fluid medication is held, a needle through which fluid medication is injected, and a plunger;

a converter body having an engagement end and an outward end;

a self-locking receiver formed in the converter body; said receiver being engaged with a plunger end of the injection cartridge; said receiver including a receiver receptacle which opens at the engagement end and has inwardly facing surfaces;

at least one self-locking constriction formed along the inwardly facing surfaces of the receiver receptacle; said at least one constriction being sized to allow insertion of said plunger end of the injection cartridge; said at least one constriction further being sized to engage outward surfaces of the injection cartridge along the plunger end thereof to develop restraining forces between the injection cartridge and said at least one constriction from insertion of the plunger end into the receptacle to provide a self-locking action between the cartridge and converter body when the cartridge is inserted into the receiver;

wherein the at least one self-locking constriction includes an inwardly facing approximately conical surface which converges inwardly advancing into the receptacle;

a shaft aperture formed in the converter body and passing through the outward end thereof;

a plunger shaft connected to the plunger and extending through the shaft aperture.

2. A medicine injection syringe assembly according to claim 1 and further comprising at least one grip feature formed upon outer surfaces of the converter body.

3. A medicine injection syringe assembly, comprising:

an injection cartridge having an ampule in which fluid medication is held, a needle through which fluid medication is injected, and a plunger;

a converter body having a proximal end and a distal end;

a self-locking receiver formed by said converter body; said self-locking receiver having a receptacle which opens at said proximal end, the receptacle being configured to receive and tightly secure the injection cartridge when a plunger end of the cartridge is inserted into the receptacle; said plunger end being engaged by the self-locking receiver to secure the injection cartridge to the converter body;

wherein the receptacle is conically shaped and configured such that a plunger end of the injection cartridge can be wedged tightly into the receptacle;

a shaft aperture opening into the receptacle and being configured to allow insertion of a plunger shaft therethrough;

a plunger shaft connected to the plunger and extending through the shaft aperture.

4. A medicine injection syringe assembly according to claim 3 and further comprising one or more gripping members upon outer surfaces of the converter body for gripping by one or more fingers of a human hand.

5. A medicine injection syringe assembly according to claim 3 wherein the receptacle has inward surfaces which converge advancing into the receptacle; said inward surfaces converging at a convergence angle less than 5° of arc.

6. A medicine injection syringe assembly according to claim 3 wherein the receptacle has inward surfaces which converge advancing into the receptacle; said inward surfaces converging at a convergence angle less than 2° of arc.

7. A medicine injection syringe assembly according to claim 3 wherein the receptacle has inward surfaces which converge advancing into the receptacle; said inward surfaces converging at a convergence angle in the approximate range of 0.05°–1° of arc.

8. A medicine injection syringe assembly according to claim 3 wherein the converter body is an integral piece.

9.

10. A medicine injection syringe assembly according to claim 3 wherein the receiver has receiver sidewalls with wall thickness generally less than 0.1 inch.

11. A medicine injection syringe assembly according to claim 3 wherein the receiver has receiver sidewalls with wall thickness generally less than 0.05 inch.

12. A medicine injection syringe assembly according to claim 3 wherein the receiver has receiver sidewalls with wall thickness generally less than 0.03 inch.

13. A medicine injection syringe assembly according to claim 3 wherein the receiver has receiver sidewalls with wall thickness in the range of approximately 0.01–0.03 inch.

14. A medicine injection syringe assembly, comprising:

an injection cartridge having an ampule in which fluid medication is held, a needle through which fluid medication is injected, and a plunger;

a converter body having a proximal end and a distal end;

a self-locking receiver formed by said converter body; said self-locking receiver having a receptacle which opens at said proximal end, the receptacle being configured to receive and tightly secure the injection cartridge when a plunger end of the cartridge is inserted into the receptacle; said plunger end being engaged by the self-locking receiver to secure the injection cartridge to the converter body;

wherein the receiver has receiver sidewalls which distort in response to insertion of an injection cartridge therein to assist in performing a self-locking function;

a shaft aperture opening into the receptacle and being configured to allow insertion of a plunger shaft therethrough;

a plunger shaft connected to the plunger and extending through the shaft aperture.

15. A medicine injection syringe assembly according to claim 14 and further comprising one or more gripping members upon outer surfaces of the converter body for gripping by one or more fingers of a human hand.

16. A medicine injection syringe assembly according to claim 14 wherein the receptacle is configured such that a plunger end of an injection cartridge is wedged tightly into the receptacle as a result of inserting said plunger end into the receptacle.

17. A medicine injection syringe assembly according to claim 14 wherein the receptacle is conically shaped and configured such that a plunger end of the injection cartridge can be wedged tightly into the receptacle.

18. A medicine injection syringe assembly according to claim 14 wherein the receptacle has a cross-sectional area which decreases into the receptacle.

19. A medicine injection syringe assembly according to claim 14 wherein the receptacle has inward surfaces which converge advancing into the receptacle.

20. A medicine injection syringe assembly according to claim 14 wherein the receptacle has inward surfaces which converge advancing into the receptacle, said inward surfaces converging at a convergence angle less than 5° of arc.

21. A medicine injection syringe assembly according to claim 14 wherein the receptacle has inward surfaces which converge advancing into the receptacle, said inward surfaces converging at a convergence angle less than 2° of arc.

22. A medicine injection syringe assembly according to claim 14 wherein the receptacle has inward surfaces which converge advancing into the receptacle, said inward surfaces converging at a convergence angle in the approximate range of 0.05°–1° of arc.

23. A medicine injection syringe assembly according to claim 14 wherein the receptacle has inward surfaces which converge advancing into the receptacle, said receptacle having increasing convergence advancing into the receptacle.

24. A medicine injection syringe assembly according to claim 14 wherein the receptacle has inward surfaces which converge advancing into the receptacle, said receptacle having at least two convergence regions having increasing convergence advancing into the receptacle.

25. A medicine injection syringe assembly according to claim 14 wherein the converter body is an integral piece.

26. A medicine injection syringe assembly according to claim 14 wherein the receiver has receiver sidewalls with wall thickness generally less than 0.1 inch.

27. A medicine injection syringe assembly according to claim 14 wherein the receiver has receiver sidewalls with wall thickness generally less than 0.05 inch.

28. A medicine injection syringe assembly according to claim 14 wherein the receiver has receiver sidewalls with wall thickness generally less than 0.03 inch.

29. A medicine injection syringe assembly according to claim 14 wherein the receiver has receiver sidewalls with wall thickness in the range of approximately 0.01–0.03 inch.

30. A medicine injection syringe assembly according to claim 14 wherein the self-locking receiver further includes inwardly projecting extensions formed along said receiver sidewalls.

31. A medicine injection syringe assembly according to claim 14 wherein the converter further comprises a dose regulator for regularizing the amount of fluid injected from the syringe assembly.

32. A medicine injection syringe assembly according to claim 14 wherein the converter further comprises a dose regulator for regularizing the amount of fluid injected from the syringe assembly; said dose regulator having at least one removable stop.

33. A medicine injection syringe assembly according to claim 14 wherein the converter further comprises a dose regulator for regularizing the amount of fluid injected from the syringe assembly; said dose regulator having at least one removable stop; at least one removable stop being connected to the plunger shaft.

34. A medicine injection syringe assembly according to claim 14 wherein the converter further comprises a dose regulator for regularizing the amount of fluid injected from the syringe assembly; said dose regulator having at least one removable stop; at least one removable stop being connected to the converter body.

35. A medicine injection syringe assembly according to claim 14 wherein the converter further comprises a dose regulator for regularizing the amount of fluid injected from the syringe assembly; said dose regulator having a plurality of stops which limit the travel of the plunger shaft.

36. A medicine injection syringe assembly according to claim 14 wherein the converter further comprises a dose regulator for regularizing the amount of fluid injected from the syringe assembly; said dose regulator having a plurality of removable stops which limit the travel of the plunger shaft.

* * * * *

UNITED STATES PATENT AND TRADEMARK OFFICE
CERTIFICATE OF CORRECTION

PATENT NO.  : 5,833,669
DATED       : November 10, 1998
INVENTOR(S) : Ronald E. Wyrick It is certified that error appears in the above-identified patent and that said Letters Patent is hereby corrected as shown below:

Column 7,
Line 62 delete "range of approximately".

Column 19,
Line 48 of the patent, insert after the "9." the text of claim 9 as follows:

--A medicine syringe assembly according to claim 3 wherein the receiver has receiver sidewalls which distort in response to insertion of an injectin cartridge therein to assist in performing a self-locking function.--

At the end of column 22 the following omitted claims are inserted:

--37. A medicine injection syringe assembly according to claim 3 wherein the converter further comprises: a dose regulator for regularizing the amount of fluid injected from the syringe assembly.

38. A medicine injection syringe assembly according to claim 3 wherein the converter further comprises: a dose regulator for regularizing the amount of fluid injected from the syringe assembly; said dose regulator having at least one removable stop.

39. A medicine injection syringe assembly according to claim 3 wherein the converter further comprises: a dose regulator for regularizing the amount of fluid injected from the syringe assembly; said dose regulator having at least one removable stop; at least one removable stop being connected to the plunger shaft.

UNITED STATES PATENT AND TRADEMARK OFFICE
CERTIFICATE OF CORRECTION

PATENT NO. : 5,833,669
DATED : November 10, 1998
INVENTOR(S) : Ronald E. Wyrick

It is certified that error appears in the above-identified patent and that said Letters Patent is hereby corrected as shown below:

40. A medicine injection syringe assembly according to claim 3 wherein the converter further comprises: a dose regulator for regularizing the amount of fluid injected from the syringe assembly; said dose regulator having a plurality of stops which limit the travel of the plunger shaft.

41. A medicine injection syringe assembly according to claim 3 wherein the converter further comprises: a dose regulator for regularizing the amount of fluid injected from the syringe assembly; said dose regulator having a plurality of removable stops which limit the travel of the plunger shaft.--

Signed and Sealed this

Third Day of July, 2001

*Attest:*

*Attesting Officer*

NICHOLAS P. GODICI
*Acting Director of the United States Patent and Trademark Office*